United States Patent
Borowicz

(10) Patent No.: US 10,265,506 B2
(45) Date of Patent: Apr. 23, 2019

(54) VASCULAR ACCESS DEVICES AND METHODS

(71) Applicant: Quick Snap Medical Supply, LLC, Minneapolis, MN (US)

(72) Inventor: Jared Michael Borowicz, Hudson, WI (US)

(73) Assignee: Quick Snap Medical Supply, LLC, Minneapolis, MN (US)

( * ) Notice: Subject to any disclaimer, the term of this patent is extended or adjusted under 35 U.S.C. 154(b) by 780 days.

(21) Appl. No.: 14/612,043

(22) Filed: Feb. 2, 2015

(65) Prior Publication Data

US 2016/0220790 A1  Aug. 4, 2016

(51) Int. Cl.
| A61M 25/06 | (2006.01) |
| A61M 5/32 | (2006.01) |
| A61M 5/158 | (2006.01) |
| A61M 39/10 | (2006.01) |

(52) U.S. Cl.
CPC ...... *A61M 25/0606* (2013.01); *A61M 5/3243* (2013.01); *A61M 25/065* (2013.01); *A61M 2005/1585* (2013.01); *A61M 2005/1587* (2013.01); *A61M 2039/1072* (2013.01)

(58) Field of Classification Search
CPC ............ A61M 25/0606; A61M 25/065; A61M 2005/1585; A61M 2005/1587; A61M 39/1072
See application file for complete search history.

(56) References Cited

U.S. PATENT DOCUMENTS

| 5,064,416 | A | 11/1991 | Newgard et al. |
| 5,935,110 | A | 8/1999 | Brimhall |
| 6,056,718 | A * | 5/2000 | Funderburk ...... A61M 25/0097 604/161 |
| 6,719,726 | B2 | 4/2004 | Meng et al. |
| 7,798,994 | B2 | 9/2010 | Brimhall |
| 2009/0062744 | A1* | 3/2009 | Weilbacher ........... A61M 5/158 604/192 |
| 2012/0197204 | A1* | 8/2012 | Helm, Jr. ............. A61M 25/02 604/176 |

OTHER PUBLICATIONS

"B. Braun Introcan Saftety IV Catheter," B. Braun Medical Inc., 2009, 4 pages.
"BD Insyte Autoguard BC," Wolf Medical Supply, 2011, 2 pages.
"Introcan Saftety 3," B. Braun Medical Inc., 2014, 6 pages.

* cited by examiner

*Primary Examiner* — Nathan R Price
*Assistant Examiner* — Justin L Zamory
(74) *Attorney, Agent, or Firm* — Fish & Richardson P.C.

(57) ABSTRACT

Some embodiments of a vascular access device are configured to reduce the likelihood of blood leakage during installation, even when the device is optionally installed using a single hand. In particular implementations, the vascular access device is configured as a peripheral intravenous (IV) device.

8 Claims, 4 Drawing Sheets

VASCULAR ACCESS DEVICES AND METHODS

TECHNICAL FIELD

This document relates to devices and methods for vascular access, such as a peripheral intravenous (IV) device and method.

BACKGROUND

There are numerous ways and reasons to access a patient's vasculature. Patients may need administration of IV therapy for hydration, antibiotics, other medications, chemotherapy, blood products, and the like. The type of vascular access device will depend on the patient, diagnosis length of time needed, lifestyle, healthcare worker's preference, patient's ability and preference, what the device is being used for, and difficulties relating to using or maintaining the device.

Some peripheral IV devices provide access through a skin opening using a cannula-over-needle assembly, in which a flexible plastic cannula is slidably mounted over a metal introducer needle. After the tip of the introducer needle and cannula are positioned into the patient's targeted blood vessel via venipuncture, the tip of the cannula is advanced inside the vessel over the needle to the appropriate position and secured. The introducer needle is then withdrawn and discarded while the flexible cannula is retained in its position to provide fluid communication with the targeted vessel. In some emergency treatment circumstances, blood may seep from the vessel, through the cannula, and possibly out of the proximal end of the access device (after the introducer needle is withdrawn). A user may reduce the likelihood of such blood seepage by applying finger pressure (with a first hand of the user) to the patient's skin near the targeted vessel (e.g., a tamponade) until a secondary instrument can be assembled to the proximal end of the access device (using a second hand of the user).

SUMMARY

The innovative vascular access device concepts provided herein can be adapted for implementation in various medical device designs such as, but not limited to, peripheral IV catheters, central percutaneous IV catheters, and peripherally inserted central catheters (PICC lines). In some embodiments, the vascular access device is configured to reduce the likelihood of blood leakage during installation, even when the device is installed using a single hand (without requiring an additional hand of the user to apply a tamponade). For example, the vascular access device may be configured as a peripheral IV catheter assembly (e.g., including an access cannula device and an introducer needle) that is readily penetrated through a skin surface and into a targeted vessel, and a repeatably penetratable septum housed in the access cannula device can prevent blood flow to the proximal end of the access cannula device during and after withdrawal of the introducer needle. Moreover, in this example, the user may—optionally, with a single hand—withdraw an introducer needle from the assembly and install a secondary instrument at the proximal end of the access cannula device that is configured to penetrate the septum for fluid communication between the targeted vessel and the secondary instrument.

Some implementations of a vascular access device may include a catheter assembly, a needle introducer assembly, and a connector assembly. The catheter assembly may include a catheter hub, a catheter tube, and a septum. The catheter tube may be attached to (and extend from) the catheter hub. Also, the septum may be disposed within an interior space defined by the catheter hub. The introducer needle assembly may include an introducer needle hub, an introducer needle, and a needle guard. The introducer needle may be attached to (and extend from) the introducer needle hub. Also, the introducer needle may be configured to penetrate through the septum and to extend distally of a distal end of the catheter tube. The introducer needle may be slidably withdrawable from the septum and the catheter tube. The connector assembly may include a connector body and a connector needle attached to and extending from the connector body. The connector body may be configured to mate with the catheter hub after withdrawal of the introducer needle assembly by pressing the connector body into engagement with the catheter hub so that the connector needle penetrates the septum.

Additional implementations described herein may include a method of installing a vascular access device. The method may include piercing a distal tip of an introducer needle through a skin surface and positioning the distal tip in a blood vessel while the introducer needle is slidably disposed with a lumen of a catheter assembly such that a distal tip of the catheter assembly is also positioned in the blood vessel. Also, the method may include withdrawing the introducer needle from the patient while leaving the catheter assembly positioned in the blood vessel. The introducer needle may be slidably withdrawn through a sealing septum housed within the catheter assembly such that the septum seals a blood flow path through the catheter assembly after the introducer needle disengages the septum and the catheter assembly. The method may further include mounting a connector assembly with the catheter assembly into an operative configuration by pressing a connector body of the connector assembly into engagement with a catheter hub of the catheter assembly so that a connector needle of the connector assembly penetrates through the sealing septum previously occupied by the introducer needle.

Particular implementations described herein include a vascular access device that may include a catheter assembly, an introducer needle assembly, and (optionally) a connector assembly. The catheter assembly may include a catheter hub, a catheter tube, and a septum disposed within an interior space defined by the catheter hub. Also, the introducer needle assembly may include an introducer needle, and the introducer needle may be configured to penetrate through the septum and to be slidably withdrawable from the septum. Optionally, the connector assembly may include a connector body and a connector needle attached to and extending from the connector body. The connector body may be configured to mate with the catheter hub by pressing the connector body into engagement with the catheter hub so that the connector needle penetrates the septum.

Some or all of the embodiments described herein may provide one or more of the following advantages. First, some embodiments of the vascular access devices may be configured for one-handed operation. For example, some embodiments eliminate the need for a healthcare worker to use a second hand for applying a tamponade during installation of the vascular access device. As such, the vascular access devices are both effective and efficient for healthcare workers to use, especially during emergency medical treatments where blood seepage might otherwise occur. In addition, one-handed installation allows the healthcare worker to potentially use his or her other hand to attend to other aspects of medical care treatment.

Second, some embodiments of the vascular access devices substantially prevent blood leakage during installation. Some such embodiments include a resilient septum (seal) in the catheter hub that substantially prevents blood from leaking or squirting out from the IV catheter prior to connecting the catheter hub to another device. Blood is therefore less prone to contact and contaminate gloves, clothing, shoes, bedding, floors, equipment, and exposed parts of the healthcare worker's body. Accordingly, some risks to healthcare workers associated with exposure to the patient's blood can be potentially mitigated. In addition, cleanliness of the healthcare setting is better maintained. Therefore, the time and expenses related to cleanup of the healthcare setting are reduced.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
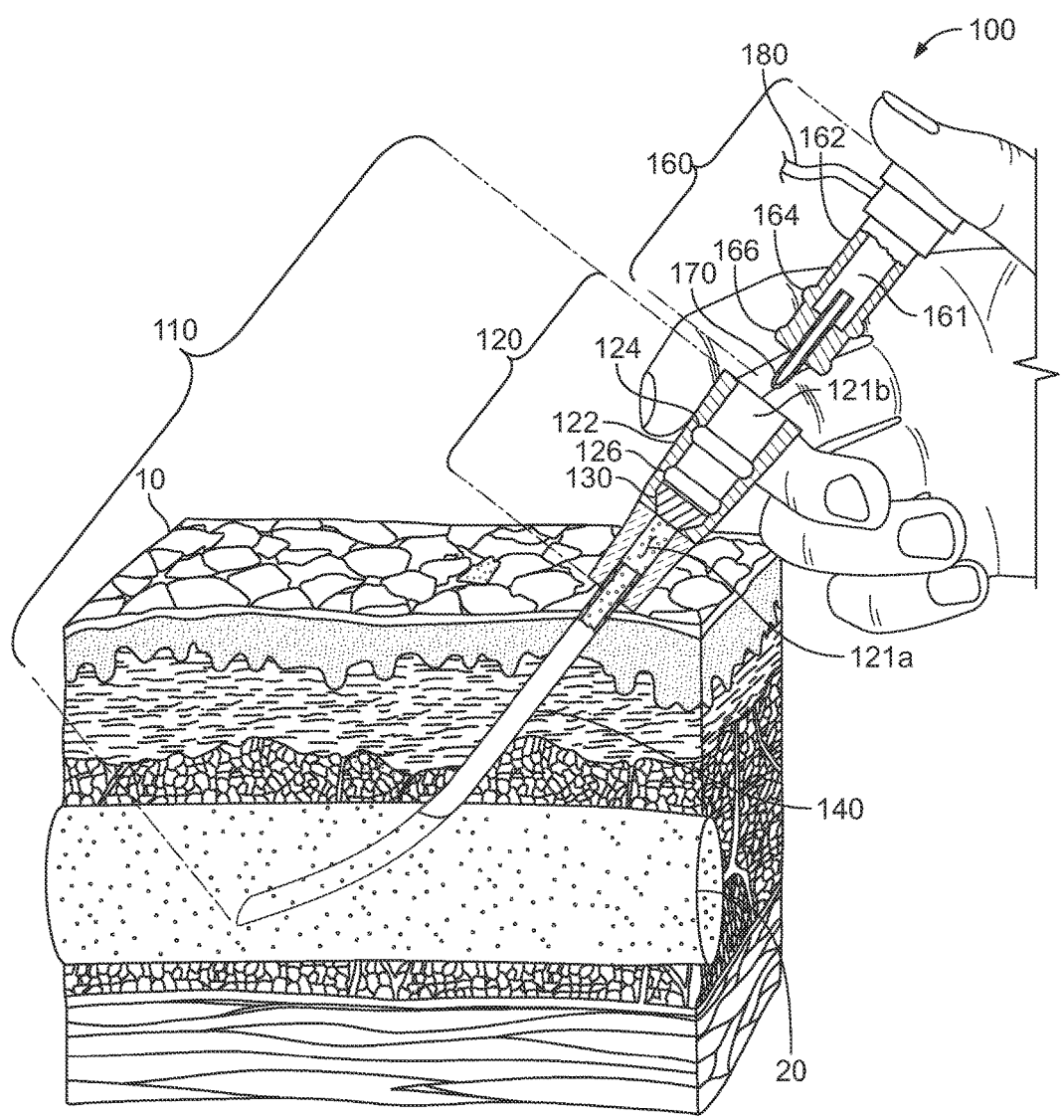
FIG. 1 is a cross-sectional side view of a vascular access device that is in the process of being installed in a patient in accordance with some embodiments.

Referring to FIG. 1, some embodiments of a vascular access device 100 can be used to access a blood vessel 20 through the skin surface 10 of a patient. The vascular access device 100 in the depicted embodiment comprises multiple components, including a catheter assembly 110, a connector assembly 160. As described further below (e.g., refer to FIG. 3A), the vascular access device 100 may also comprise other components such as an introducer needle assembly and a protective sheath for the introducer needle assembly 300. In this particular embodiment depicted in FIG. 1, the vascular access device 100 is configured as a peripheral IV catheter assembly that is readily penetrated through the skin surface 10 and into a blood vessel 20, and the catheter assembly 110 houses a penetratable sealing septum 130 that is configured to prevent blood seepage to the proximal end of the access cannula device during and after withdrawal of the introducer needle (described in more detail below in connection with FIGS. 3A-C). Also, in this particular embodiment depicted in FIG. 1, the catheter assembly 110 is configured to mate with a secondary instruments (e.g., the connector assembly 160 in this example) using a single-handed, snap-fit connection such that the septum 130 (which was previously penetrated by the introducer needle until the needle was withdrawn) is penetrated again to open a fluid path between the targeted vessel 20 and the secondary instrument 160.

In this embodiment, the connector assembly 160 is releasably attachable to the catheter assembly 110. For example, a user may simultaneously grasp the catheter assembly 110 and the connector assembly 160 with a single hand to conveniently press them together in a mating position. When the connector assembly 160 is coupled with the catheter assembly 110, and when at least a distal end portion of the catheter assembly 110 is in the blood vessel 20 (e.g., as shown), fluid communication exists between the blood vessel 20 and the connector assembly 160. Accordingly, fluids such as medications can be infused into the blood vessel 20 via the connector assembly 160. In another example usage mode, a blood sample from the blood vessel 20 can be taken via the connector assembly 160. It should be understood that the view of the skin surface 10 and blood vessel 20 are not drawn to scale (magnified for purposes of illustration in FIG. 1) relative to the vascular access device 100. Furthermore, it should be understood from the description herein that the vascular access devices 100 are scalable to a range of sizes, including adult and pediatric sizes. In some embodiments, the vascular access devices provided herein have multiple lumens As described further below, when the connector assembly 160 is not attached to the catheter assembly 110 (e.g., as shown), the septum 130 of the catheter assembly 110 is positioned to provide a seal that hinders blood seepage from the catheter assembly 110. Hence, the vascular access device 100 is configured to be installed in a patient without needing to apply a tamponade force on the skin surface 10 of the patient prior to coupling the connector assembly 160 with the catheter assembly 110. As such, the vascular access device 100 can be installed using a one-handed installation method.

Still referring to FIG. 1, the catheter assembly 110 includes a catheter hub 120 and a catheter tube 140. The catheter tube 140 is attached to and extends distally from the catheter hub 120. The catheter hub 120 comprises a female connector body 122 and a resilient septum 130 disposed therein. The resilient septum 130 is arranged within an interior space defined by the female connector body 122 such that the interior space is divided into a distal interior space 121a and a proximal interior space 121b, with the resilient septum 130 located therebetween.

The catheter tube 140 defines at least one lumen. The at least one lumen of the catheter tube 140 conflates with the distal interior space 121a defined by the catheter hub 120. Accordingly, fluid communication can exist from the blood vessel 20, through the catheter tube 140, to the distal interior space 121a. As described further below, the resilient septum 130 is configured to occlude fluid flow through the catheter assembly 110 when the connector assembly 160 is decoupled from the catheter assembly 110. That is, while the distal interior space 121a of the catheter hub 120 is confluent with the catheter tube 140, the proximal interior space 121b is not in fluid communication with the catheter tube 140 when the connector assembly 160 is decoupled from the catheter assembly 110. However, when the connector assembly 160 is coupled with the catheter assembly 110, the resilient septum 130 is pierced by the connector assembly 160, and then fluid flow through the vascular access device 100 is facilitated.

The connector assembly 160 includes a male connector body 162, a connector needle 170, and a connector tube 180. The connector needle 170 is attached to and extends distally from the male connector body 162. The connector needle 170 defines at least one lumen. The at least one lumen of the connector needle 170 conflates with an open interior space 161 defined by the male connector body 162. The connector tube 180 is also attached to and extends from the male connector body 162. The connector tube 180 defines at least one lumen. The at least one lumen of the connector tube 180 conflates with the open interior space 161 defined by the male connector body 162. Accordingly, fluid communication exists from the connector needle 170, through the male connector body 162, to the connector tube 180. One of ordinary skill in the art will understand that while one end of the connector tube 180 is attached to the male connector body 162, the other end of the connector tube 180 can be attached to a variety of types of fittings, containers, devices, and the like.

As described further below, when the connector assembly 160 is coupled with the catheter assembly 110, fluid communication exists from the connector tube 180, through the connector assembly 160 and catheter assembly 110, to the blood vessel 20. Hence, the vascular access device 100 is then functional for infusing liquids to the blood vessel 20, or withdrawing blood from the blood vessel 20. To attain such an arrangement, the connector needle 170 pierces through the resilient septum 130. Liquids can then freely flow through vascular access device 100, rather than being occluded by the resilient septum 130.

Figure 2A:
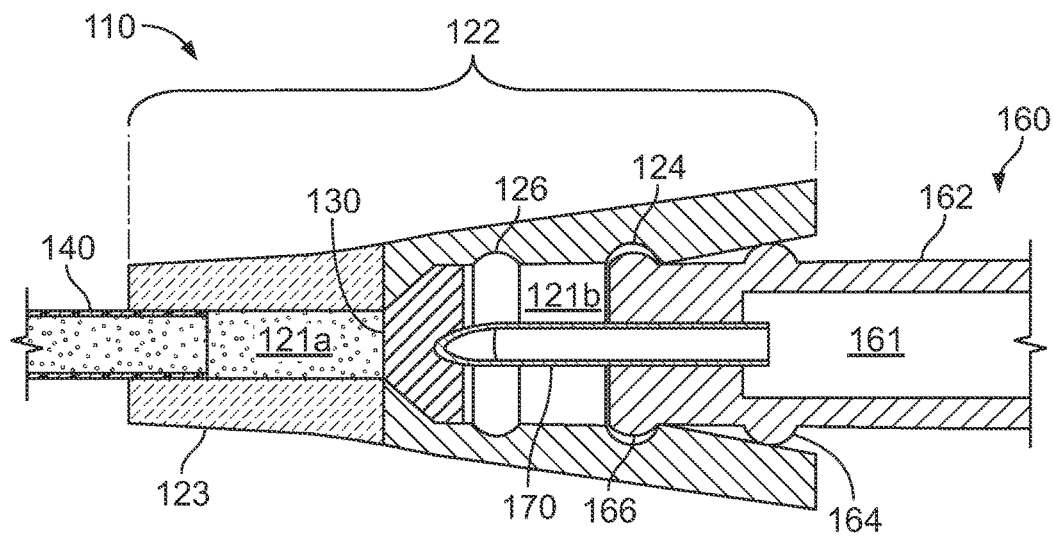
FIGS. 2A-B are cross-sectional side views of a portion of the vascular access device of FIG. 1.
Figure 2B:
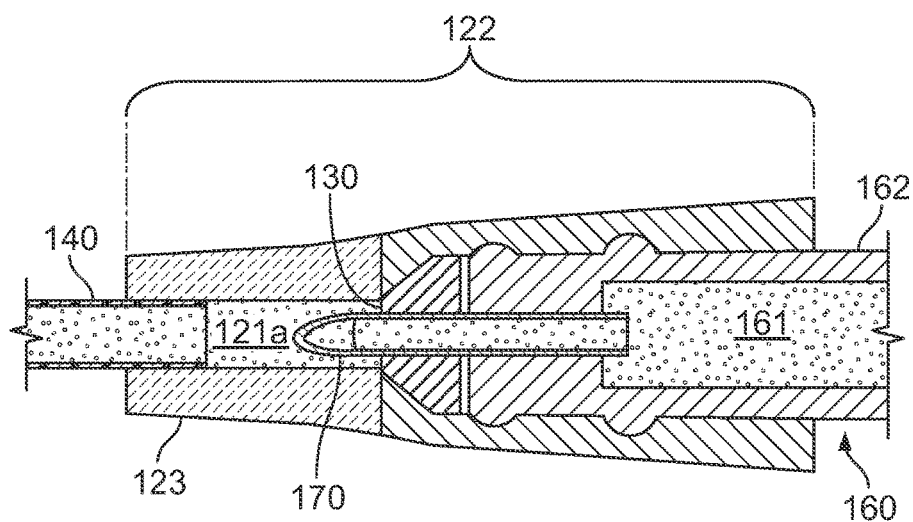

Referring now also to FIGS. 2A-B, some embodiments of the connector assembly 160 can be configured to provide a snap-fit, sealing engagement with the catheter assembly 110. While FIG. 1 shows the connector assembly 160 entirely decoupled from the catheter assembly 110, FIG. 2A shows the connector assembly 160 partially mated with the catheter assembly 110, and FIG. 2B shows the connector assembly 160 fully mated with the catheter assembly 110. Hence, the series of those three figures are provided to describe the process of coupling the connector assembly 160 with the catheter assembly 110.

When the connector assembly 160 is entirely decoupled the catheter assembly 110, even though the distal end portion of the catheter tube 140 is the blood vessel 20, the resilient septum 130 seals the catheter assembly 110 so that no blood leaks from the catheter assembly 110 (refer to FIG. 1). To begin the process of coupling the connector assembly 160 with the catheter assembly 110, in some embodiments a healthcare worker presses the male connector body 162 into the female connector body 122. In result, the tip of the connector needle 170 is forced to begin piercing the resilient septum 130 (refer to FIG. 2A). In some embodiments, the proximal interior space 121b is vented to provide a pathway to relieve air pressure from proximal interior space 121b that may build up as the male connector body 162 is pressed into the female connector body 122.

When the process of coupling the connector assembly 160 with the catheter assembly 110 is completed, the tip of the connector needle 170 has been forced all the way through the resilient septum 130 (refer to FIG. 2B). In the fully coupled configuration, the distal interior space 121a of the catheter hub 120 is in fluid communication with the interior space 161 of the male connector body 162. Accordingly, the vascular access device 100 is then functional for infusing liquids to the blood vessel 20, or withdrawing blood from the blood vessel 20.

In some embodiments, the piercing of the resilient septum 130 by the connector needle 170 is accomplished without causing and/or resulting in deflection of the resilient septum 130. Rather, in some such embodiments the piercing of the resilient septum 130 by the connector needle 170 results in a compression of the resilient septum 130. Alternatively, in some embodiments the piercing of the resilient septum 130 by the connector needle 170 causes deflection of the resilient septum 130.

In the depicted embodiment, the coupling of the male connector body 162 with the female connector body 122 can take place by pressing and snapping the male connector body 162 into the female connector body 122. That is, an axial compression force, such as a force applied by the thumb of a healthcare worker (refer to FIG. 1), can cause the male connector body 162 to be pressed and snapped into a fully seated arrangement with the female connector body 122. Accordingly, the coupling of the male connector body 162 with the female connector body 122 can be performed using a one-handed technique. Once fully seated, the arrangement can provide a substantial resistance to decoupling so as to meeting all applicable standards and regulatory requirements for such a device.

To facilitate a snap-together engagement technique, in some embodiments the male connector body 162 and the female connector body 122 have complementary structural features that snap into engagement with each other. For example, in the depicted embodiment the male connector body 162 has a proximal annular protrusion 164 and a distal annular protrusion 166. The female connector body 122, in turn, has a proximal annular recess 124 and a distal annular recess 126. As best seen in FIG. 2B, the proximal annular recess 124 receives the proximal annular protrusion 164, and the distal annular recess 126 receives the distal annular protrusion 166. When the proximal annular protrusion 164 is seated in the proximal annular recess 124, and the distal annular protrusion 166 is seated in the distal annular recess 126, the tip of the connector needle 170 has been forced all the way through the resilient septum 130, and the vascular access device 100 is functional for infusing liquids to the blood vessel 20 or withdrawing blood from the blood vessel 20. While in the depicted embodiment the male connector body 162 and the female connector body 122 have two complementary annular protrusions/recesses, in some embodiments only one complementary annular protrusion/recess is included. In some embodiments, three or more complementary annular protrusions/recesses are included.

While the depicted embodiment facilitates snap-together coupling between the male connector body 162 and the female connector body 122, in some embodiments the male connector body 162 and the female connector body 122 are configured to be coupled together in other manners. For example, in some embodiments the male connector body 162 and the female connector body 122 are configured to be coupled together in manners such as, but not limited to, screwing together, pivoting together, laterally sliding together (e.g., using a dovetail or tongue-in-groove arrangement), and the like, and combinations thereof.

Still referring to FIGS. 1 and 2A-B, the catheter assembly 110 includes the female connector body 122, the resilient septum 130, and the catheter tube 140. These components can be attached to each other using various techniques. For example, in some embodiments one or more of the female connector body 122, the resilient septum 130, and the catheter tube 140 are joined to each other using an adhesive. In some embodiments, one or more of the female connector body 122, the resilient septum 130, and the catheter tube 140 are joined to each other using a heat-staking technique. In some embodiments, one or more of the female connector body 122, the resilient septum 130, and the catheter tube 140 are joined to each other by a molding process (e.g., insert molding, overmolding, and the like). In some embodiments, other joining techniques, such as, but not limited to ultrasonic welding, solvent bonding, radio-frequency welding, press-fitting, pinning, and the like, and combinations thereof, are used to join one or more of the female connector body 122, the resilient septum 130, and the catheter tube 140 to each other.

In some embodiments, the female connector body 122 comprises a flexible material such as, but not limited to, silicone, high durometer rubber, polyurethane, styrenics, copolyesters, polyamides, polyolefin blends, polyolefin alloys, reactor TPOs, polyolefin plastomers, polyolefin elastomers, and the like. The relative flexibility of the female connector body 122 (as compared to the male connector body 162) can facilitate the snap-together coupling between the male connector body 162 and the female connector body 122. For example, in some embodiments as the male connector body 162 is pressed into the female connector body 122, the female connector body 122 can flex, stretch, and/or expand to allow the proximal annular protrusion 164 and the distal annular protrusion 166 to pass through on their way to being seated in the proximal annular recess 124 and the distal annular recess 126.

Optionally, in some embodiments, the female connector body 122 has wings with suture attachment holes/features for securement of the female connector body 122 to the skin 10 of the patient. In some embodiments, the female connector body 122 does not include wings. In particular embodiments, the female connector body 122 is color-coded in correspondence with the size (e.g., gauge and/or length) of the catheter tube 140.

The female connector body 122 includes a distal end portion 123. In some embodiments, the distal end portion 123 comprises a transparent or essentially transparent material. In some embodiments, the distal end portion 123 includes one or more transparent or essentially transparent window portions. While in some embodiments the distal end portion 123 is made of a different material than the rest of the female connector body 122, in some embodiments the distal end portion 123 is made of the same material as the rest of the female connector body 122. The transparency of at least a portion of the distal end portion 123 facilitates visualization by a healthcare worker of the presence of blood in distal interior space 121a, which is known as flashback detection. Flashback detection facilitates confirmation that at least the distal end portion of the catheter tube 140 is within a blood vessel as desired.

The catheter assembly 110 also includes the resilient septum 130. In some embodiments, the resilient septum 130 comprises a flexible material such as, but not limited to, silicone, polyurethane, rubber, nitrile rubber, polytetrafluoroethylene, and the like. In some embodiments, the resilient septum 130 comprises a biocompatible gel or semi-solid material.

The catheter assembly 110 also includes the catheter tube 140. In some embodiments, the catheter tube 140 comprises polyurethane, fluorinated ethylene propylene (FEP), silicones, nylon, nitinol, and the like. In some embodiments, the catheter tube 140 is treated to increase its lubricity.

The connector assembly 160 includes the male connector body 162, the connector needle 170, and the connector tube 180. The components of the connector assembly 160 can be attached together using any of the techniques described above in reference to the catheter assembly 110.

In some embodiments, the male connector body 162 can comprise a material such as polycarbonate, polyvinylchloride, polyurethanes, silicones, other thermoplastic elastomers, and the like. In particular embodiments, the male connector body 162 is transparent or essentially transparent. As such, the open interior space 161 can serve as a flash chamber to assist the healthcare worker to detect a proper result during the process of coupling the connector assembly 160 with the catheter assembly 110. In the depicted embodiment, the proximal annular protrusion 164 and the distal annular protrusion 166 are integral structural features of the male connector body 162 that have been molded in a unitary manner with the other portions of the male connector body 162. In some embodiments, the proximal annular protrusion 164 and/or the distal annular protrusion 166 are distinguished from the other portions of the male connector body 162 by virtue of being made from another type of material. For example, in some embodiments the proximal annular protrusion 164 and/or the distal annular protrusion 166 are ring components that get attached to the other portions of the male connector body 162. Consequently, in some embodiments the proximal annular protrusion 164 and/or the distal annular protrusion 166 can be made of a different material than the other portions of the male connector body 162 are made of. For example, in some such embodiments the proximal annular protrusion 164 and/or the distal annular protrusion 166 are made of a softer or more flexible material than the other portions of the male connector body 162.

The connector assembly 160 also includes the connector needle 170. The connector needle 170 can comprise a material such as, but not limited to, stainless steel, steel alloys, polymeric materials, and the like. In the depicted embodiment, the connector needle 170 has a non-coring needle tip design. For example, the opening at the tip of the connector needle 170 faces radially outward (rather than axially outward). Accordingly, when a healthcare worker presses the male connector body 162 into the female connector body 122, the tip of the connector needle 170 can pierce through the resilient septum 130 without creating a core (plug) that could occlude the connector needle 170. In some embodiments, the connector needle 170 may include one or more barbs.

The connector assembly 160 also includes the connector tube 180. One of ordinary skill in the art will understand that while one end of the connector tube 180 is attached to the male connector body 162, the other end of the connector tube 180 can be attached to a variety of types of fittings, containers, devices, and the like.

Figure 3A:
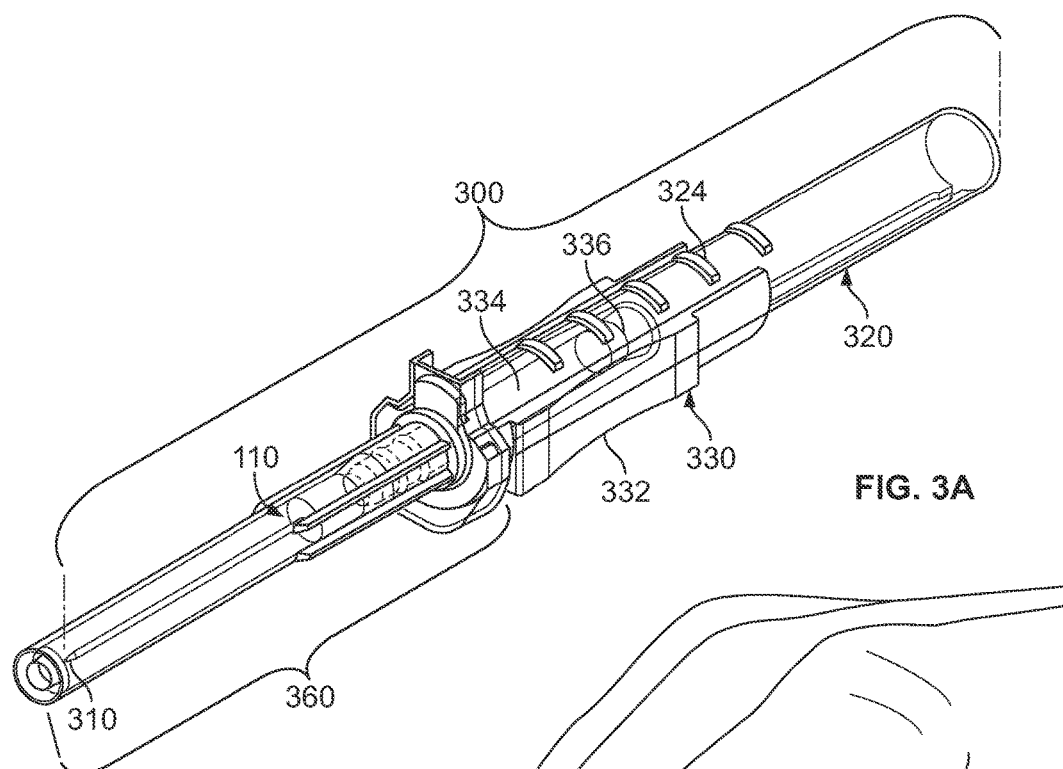
FIGS. 3A-C are perspective views of the vascular access device of FIG. 1 during an example process of using the vascular access device, in accordance with some embodiments.
Figure 3B:
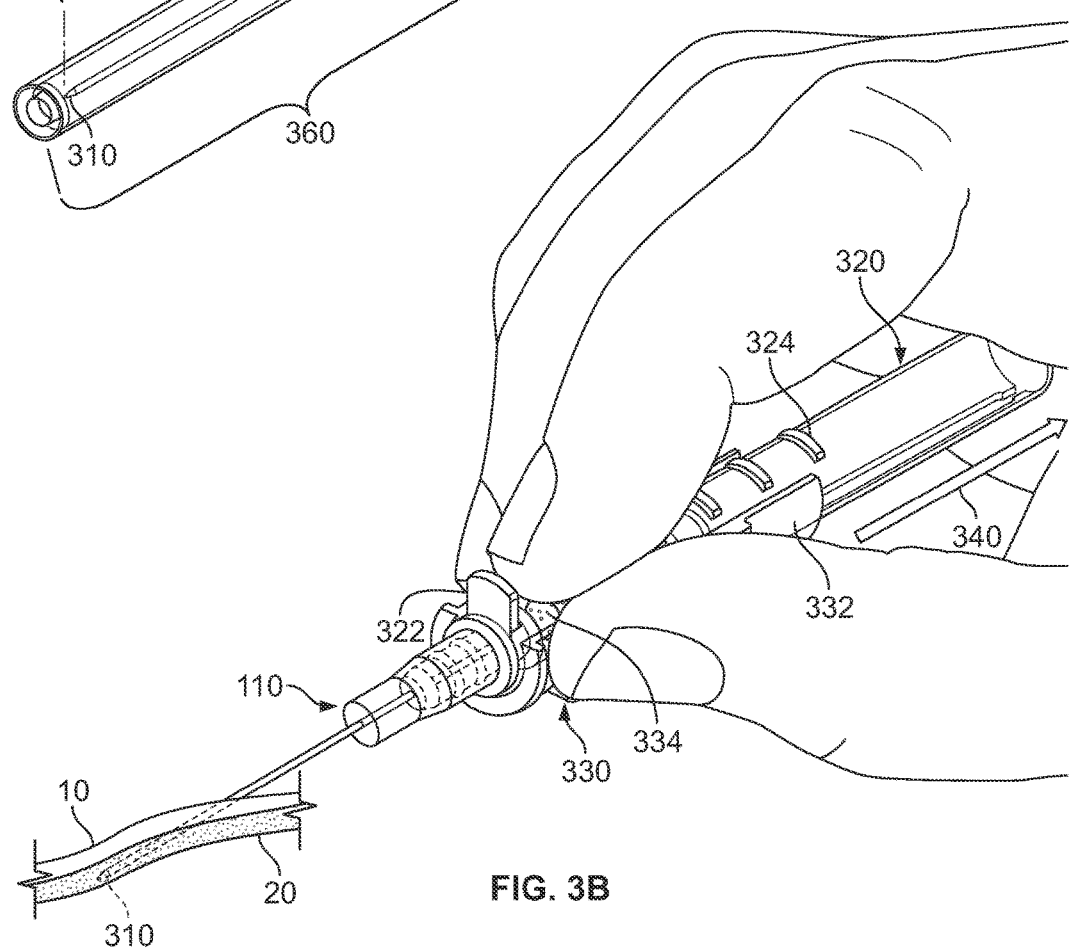
Figure 3C:
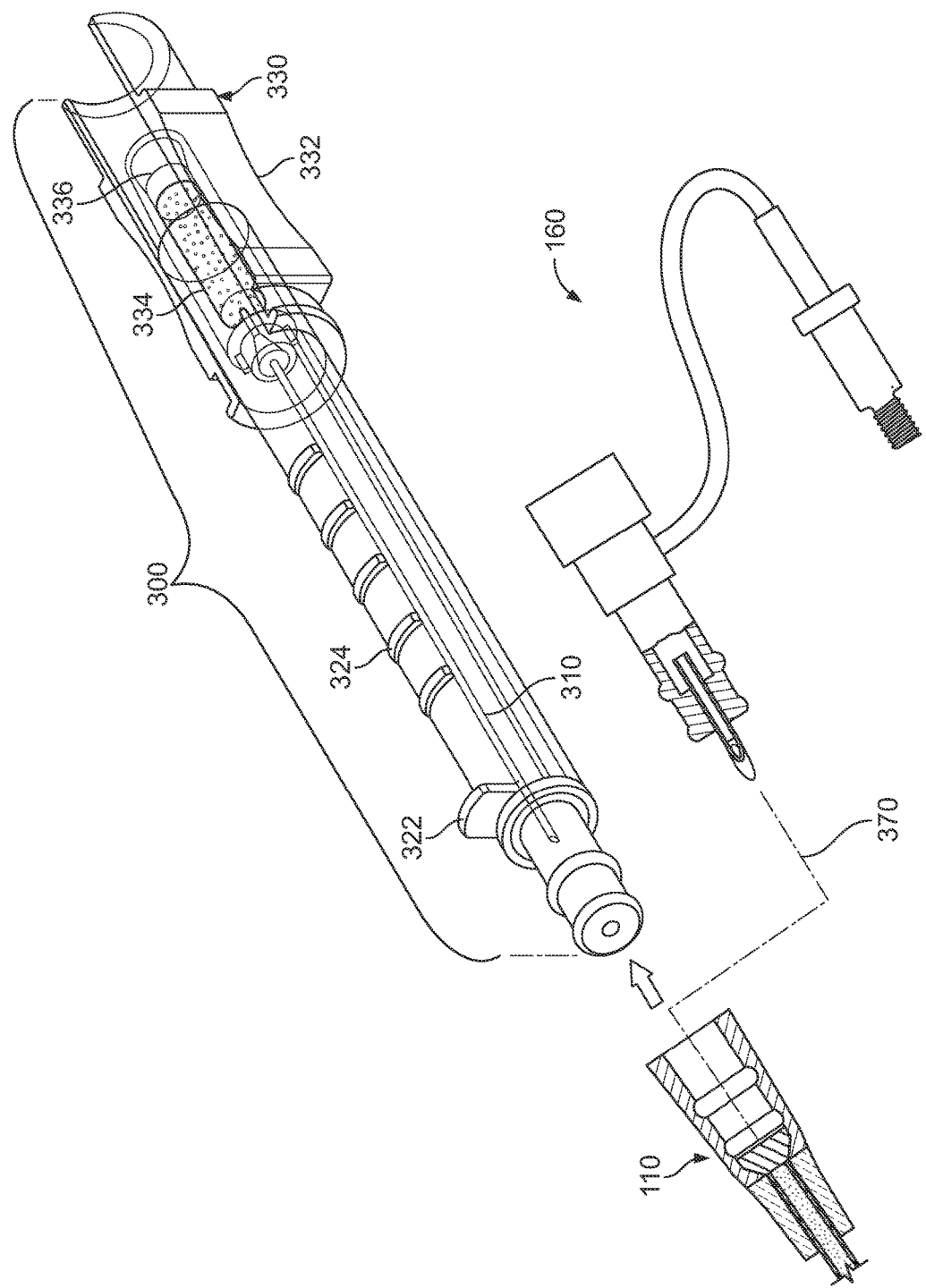

Referring now to FIGS. 3A-C, the vascular access device 100 can include a combination of the catheter assembly 110, a secondary instrument (such as the connector assembly 160 in this embodiment), and the introducer needle assembly 300 (which can removably pre-installed within the catheter assembly 110 as part of a packaged kit). As previously described, the secondary instrument (such as the connector assembly 160 in this embodiment) can be releasably mated to the catheter assembly 110 after the introducer needle assembly 300 is withdrawn. As described further herein, some embodiments of the installation method can be performed by the healthcare worker, optionally, using a single hand.

In this embodiment, the introducer needle assembly 300 and/or the catheter assembly 110 are coupled with a protective sheath 360 that is configured to cover at least the sharp tip of the introducer needle. The introducer needle assembly 300 and the protective sheath 360 as shown in FIG. 3A are configured together as a healthcare worker would receive and initially handle them (other than sterile packaging, not shown) prior to installing the vascular access device 100. The protective sheath 360 covers the introducer needle assembly 300 to reduce the likelihood of accidental needle sticks. Prior to installing the catheter assembly 110 into the patient using the introducer needle assembly 300, the healthcare worker removes the protective sheath 360 and discards it.

In this embodiment, the introducer needle assembly 300 includes the introducer needle 310, a needle guard 320, and an introducer needle hub 330. The introducer needle 310 is fixedly coupled to and extending from the introducer needle hub 330. The introducer needle hub 330 is slidably coupled with the needle guard 320. The slidable relationship between the needle guard 320 and introducer needle hub 330 is represented by arrow 340.

As shown in FIG. 3B, the introducer needle 310 is a sharp, hollow needle that is used to pierce through the patient's skin 10 to access the blood vessel 20. The catheter assembly 110 is slidably coupled on the introducer needle 310. To install the catheter assembly 110, the healthcare worker inserts the distal tip of the introducer needle 310 through the patient's skin 10 and positions the distal tip of the introducer needle 310 in the blood vessel 20. In doing so, the distal tip of the catheter assembly 110 is also inserted into the blood vessel 20. When the distal tip of the introducer needle 310 is in the blood vessel 20, some blood will flow into the lumen of the introducer needle 310 and collect in a flash chamber 334 of the introducer needle hub 330. The rear of the flash chamber 334 is plugged by a microporous plug 336 that allows air to escape the flash chamber 334 while containing blood within the flash chamber 334. The presence of blood in the flash chamber 334 provides a visual indication to the healthcare worker that the introducer needle 310 (and the catheter assembly 110 by association) is properly positioned within the blood vessel 20.

After insertion of the introducer needle 310, the healthcare worker slides the introducer needle hub 330 away from the patient's skin 10 as indicated by arrow 340. In some embodiments, contoured portions 332 on the introducer needle hub 330 can be provided to assist the healthcare worker during this step. During the sliding of the introducer needle hub 330, the healthcare worker maintains the position of the needle guard 320 generally stationary in relation to the patient. Doing so withdraws the introducer needle 310 into the safe confines of the needle guard 320, while maintaining the catheter assembly 110 in a proper position in relation to the patient. A push-off tab 322 that is located at the distal end of the needle guard 320 and/or surface features 324 on the needle guard 320 can also be used by the healthcare worker to assist with the performance of this step. Accordingly, if desired, this step can be performed by the healthcare worker using a single hand.

When the healthcare worker has completed sliding the introducer needle hub 330 away from the patient's skin 10 as indicated by arrow 340 (such that the introducer needle 310 is fully within the needle guard 320), the healthcare worker can then separate the introducer needle assembly 300 from the catheter assembly 110 (refer to FIG. 3C). The sharp tip of the introducer needle 310 will be retained (e.g., locked) within the needle guard 320 so as to protect the healthcare worker (and others) from accidental needle sticks from a contaminated needle. The introducer needle assembly 300 can then be properly discarded while the needle 310 is safely covered.

As described above, due to the resilient septum 130 in the catheter assembly 110, essentially no blood will leak through the lumen of the catheter assembly 110 after separation of the introducer needle assembly 300 from the catheter assembly 110. Again, this feature can eliminate the need for the healthcare worker to apply a tamponade pressure on the skin surface 10 of the patient prior to coupling the connector assembly 160 with the catheter assembly 110. As such, the vascular access device 100 can be optionally installed using the previously described one-handed installation method.

The connector assembly 160 can then be coupled with the catheter assembly 110, as indicated by phantom line 370. In the depicted embodiment, the connector assembly 160 and the catheter assembly 110 are configured for snap-together coupling. Therefore, to couple the connector assembly 160 and the catheter assembly 110 together, the healthcare worker can simply press the male connector body 162 into the female connector body 122 so that the proximal annular protrusion 164 is seated in the proximal annular recess 124, and the distal annular protrusion 166 is seated in the distal annular recess 126 (refer to FIGS. 1, 2A, and 2B). This step can be performed using a one-handed installation method. When the connector assembly 160 and the catheter assembly 110 have been properly coupled together (e.g., snapped together), and the distal tip of the catheter assembly 110 is properly within the blood vessel 20, the open interior space 161 that serves as a flash chamber of the connector assembly may contain some blood. The presence of blood in the open interior space 161 is an indication to the healthcare worker that the vascular access device 100 has been properly installed.

A number of embodiments of the invention have been described. Nevertheless, it will be understood that various modifications may be made without departing from the scope of the invention. Accordingly, other embodiments are within the scope of the following claims.

What is claimed is:
1. A vascular access device comprising:
a catheter assembly comprising (i) a catheter hub, (ii) a catheter tube, and (iii) a septum, the catheter tube attached to and extending from the catheter hub, the septum disposed within an interior space defined by the catheter hub;
an introducer needle assembly comprising (a) an introducer needle hub, (b) an introducer needle, and (c) a needle guard, the introducer needle attached to and extending from the introducer needle hub, the introducer needle configured to penetrate through the septum and to extend distally of a distal end of the catheter tube, wherein the introducer needle is slidably withdrawable from the septum and the catheter tube; and
a connector assembly comprising a connector body and a connector needle attached to and extending from the connector body, the connector body configured to mate with the catheter hub after withdrawal of the introducer needle assembly by pressing the connector body into engagement with the catheter hub so that the connector needle penetrates the septum,
wherein the catheter hub comprises two annular recesses that extend along an entire circumference of the catheter hub and the connector body comprises two annular protrusions that extend around an entire circumference of the connector body, and wherein the annular recesses and the annular protrusions have configurations that are complementary with each other, and wherein the catheter hub deflects as the connector body is pressed into a mated condition with the catheter hub.
2. The vascular access device of claim 1, wherein the connector needle is configured to penetrate the septum at substantially the same location from which the introducer needle is withdrawable from the septum.

3. The vascular access device of claim 2, wherein the connector needle extends through the septum without deflecting an outer periphery of the septum.

4. The vascular access device of claim 1, wherein the connector needle is configured with a non-coring tip.

5. The vascular access device of claim 1, wherein the connector body can snap together with the catheter hub by virtue of the two annular protrusions becoming seated in the two annular recesses.

6. The vascular access device of claim 1, wherein the catheter hub deflects as the connector body is pressed into the mated condition with the catheter hub because an outer diameter of the connector body including a protrusion on the connector body is larger than an inner diameter of at least a portion of the catheter hub.

7. A vascular access device comprising:
a catheter assembly comprising (i) a catheter hub, (ii) a catheter tube, and (iii) a septum disposed within an interior space defined by the catheter hub;
an introducer needle assembly comprising an introducer needle, the introducer needle configured to penetrate through the septum and to be slidably withdrawable from the septum; and
a connector assembly comprising a connector body and a connector needle attached to and extending from the connector body, the connector body configured to mate with the catheter hub by pressing the connector body into engagement with the catheter hub so that the connector needle penetrates the septum,
wherein the connector needle extends through the septum without deflecting an outer periphery of the septum,
wherein the connector needle has a non-coring tip configured to penetrate the septum at substantially the same location from which the introducer needle is withdrawable from the septum,
wherein the catheter hub comprises two annular recesses that extend along an entire circumference of the catheter hub and the connector body comprises two annular protrusions that extend around an entire circumference of the connector body, and wherein the annular recesses and the annular protrusions have configurations that are complementary with each other, and
wherein the connector body snaps together with the catheter hub when the two annular protrusions are seated in the two annular recesses, and wherein the catheter hub deflects as the connector body is pressed into a mated condition with the catheter hub.

8. The vascular access device of claim 7, wherein the catheter hub deflects as the connector body is pressed into the mated condition with the catheter hub due to an outer diameter of the connector body including a protrusion on the connector body is larger than an inner diameter of at least a portion of the catheter hub.

* * * * *